United States Patent
Yi et al.

(10) Patent No.: US 11,690,164 B2
(45) Date of Patent: Jun. 27, 2023

(54) TECHNIQUES FOR PARTICLE BEAM THERAPY

(71) Applicant: University Of Maryland, Baltimore, Baltimore, MD (US)

(72) Inventors: Byong Yong Yi, Fulton, MD (US); Warren D. D'Souza, Timonium, MD (US); Ulrich Langner, Upton, MA (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 673 days.

(21) Appl. No.: 16/491,507

(22) PCT Filed: Mar. 8, 2018

(86) PCT No.: PCT/US2018/021541
§ 371 (c)(1),
(2) Date: Sep. 5, 2019

(87) PCT Pub. No.: WO2018/165423
PCT Pub. Date: Sep. 13, 2018

(65) Prior Publication Data
US 2020/0022248 A1  Jan. 16, 2020

Related U.S. Application Data

(60) Provisional application No. 62/468,412, filed on Mar. 8, 2017.

(51) Int. Cl.
*H05H 7/12* (2006.01)
*A61N 5/10* (2006.01)

(52) U.S. Cl.
CPC .............. *H05H 7/12* (2013.01); *A61N 5/107* (2013.01); *A61N 5/1071* (2013.01);
(Continued)

(58) Field of Classification Search
CPC .... A61N 2005/1087; A61N 2005/1095; A61N 2005/1096; A61N 5/1043; A61N 5/107;
(Continued)

(56) References Cited

U.S. PATENT DOCUMENTS 5,440,133 A * 8/1995 Moyers .................... A61N 5/10
250/492.3
5,668,371 A * 9/1997 Deasy .................. A61N 5/1042
850/1

(Continued)

OTHER PUBLICATIONS

Grözinger Sven Oliver. (2004). Volume conformal irradiation of moving target volumes with scanned ion beams (thesis). Verlag nicht ermittelbar, Erscheinungsort nicht ermittelbar. (Year: 2004).*

(Continued)

*Primary Examiner* — Thaddeus B Cox
*Assistant Examiner* — Marc D. Honrath
(74) *Attorney, Agent, or Firm* — Wolter Van Dyke Davis, PLLC; Eugene J. Molinelli; Cian O'Brien

(57) ABSTRACT

A method for beam therapy is provided. The method includes receiving first data indicating a plurality of target volumes within a target region inside a subject for particle beam therapy relative to a particle beam outlet on a gantry for directing a particle beam from a particle beam source. The method further includes moving automatically, one or more energy modulator components to reduce an energy of the particle beam and deliver the particle beam to the target region such that a Bragg Peak is delivered to at least one target volume of the plurality of target volumes. The method further includes repeating the moving automatically as the particle beam source rotates with the gantry around the subject, without changing the energy of the particle beam at the particle beam outlet, until every target volume is subjected to a Bragg Peak.

9 Claims, 15 Drawing Sheets

(52) U.S. Cl.
CPC .... *A61N 5/1081* (2013.01); *A61N 2005/1087* (2013.01); *A61N 2005/1096* (2013.01); *H05H 2007/125* (2013.01)

(58) Field of Classification Search
CPC ...... A61N 5/1071; A61N 5/1081; G21K 1/10; H05H 2007/004; H05H 2007/125; H05H 7/12
See application file for complete search history.

(56) References Cited

U.S. PATENT DOCUMENTS

| | | | | |
|---|---|---|---|---|
| 6,316,776 | B1* | 11/2001 | Hiramoto | A61N 5/1042 315/501 |
| 7,893,412 | B2* | 2/2011 | Ein-Gal | A61N 5/1042 250/492.23 |
| 8,330,132 | B2 | 12/2012 | Guertin et al. | |
| 9,245,657 | B2* | 1/2016 | Saito | G21K 1/00 |
| 2009/0296885 | A1* | 12/2009 | Boeh | A61N 5/1081 378/65 |
| 2010/0051833 | A1* | 3/2010 | Guertin | H05H 7/12 250/515.1 |
| 2011/0230754 | A1* | 9/2011 | Overweg | A61N 5/1049 600/411 |
| 2012/0097871 | A1* | 4/2012 | Guertin | H05H 7/12 250/515.1 |
| 2013/0320245 | A1* | 12/2013 | Pu | A61N 5/1042 250/505.1 |
| 2014/0091734 | A1 | 4/2014 | Gall et al. | |
| 2015/0133715 | A1* | 5/2015 | Iwata | A61N 5/1031 600/1 |
| 2018/0277276 | A1* | 9/2018 | Purwar | A61N 5/1043 |

OTHER PUBLICATIONS

Grözinger, S. O., Bert, C., Haberer, T., Kraft, G., & Rietzel, E. (2008). Motion compensation with a scanned ion beam: A technical feasibility study. Radiation Oncology, 3(1). https://doi.org/10.1186/1748-717x-3-34 (Year: 2008).*

Ding et al., Spot-Scanning Proton Arc (SPArc) Therapy: The First Robust and Delivery-Efficient Spot Scanning Proton Arc Therapy, Int J Radiation Oncol Biol Phys, 2016, pp. 1107-1116, vol. 96, No. 5.

Langer et al., A method to deliver energy modulated planar proton arc therapy (EMPPAT), Jour Proton Ther, 2017, pp. 1-11, vol. 3.

Freeman, Arc Therapy for Proton Pencil Beams, MedicalPhysicsWeb, 2014.

International Search Report and Written Opinion for International Patent Application No. PCT/US18/21541 dated Jul. 11, 2018, pp. 1-10.

* cited by examiner

Smallest field size

TECHNIQUES FOR PARTICLE BEAM THERAPY

CROSS-REFERENCE TO RELATED APPLICATIONS

This application is a 371 national stage application of PCT Application No. PCT/US18/21541, filed Mar. 8, 2018, and claims benefit of Provisional Application No. 62/468,412, filed Mar. 8, 2017, the entire contents of each of which are hereby incorporated by reference as if fully set forth herein, under 35 U.S.C. § 119(e).

BACKGROUND

The use of proton and other particle beam therapy for treating cancer has greatly increased over the past decade, mostly because of the advantageous interaction properties of particle beams. A particle beam initially deposits a relatively low dose upon entering the patient, and the deposited dose rises to a sharp maximum, known as the Bragg Peak, near the end of the beam's range in the patient and produces no exit beam. The sharp Bragg Peak and the finite range of the beam provide the ability to deliver a highly conformal treatment, allowing for dose escalation to the tumor and/or a reduction of exposure to the surrounding healthy tissues. The depth of the Bragg Peak, also called the beam range, depends on the energy of the particles in the particle beam entering the patient. There has been a recognized need for a method of modulating the in vivo beam range to improve the ability to fully exploit the advantages of particle beam therapy, such as proton radiation therapy. This is typically done by modifying the particle source to output beams of different particle energies, or modifying magnetic fields in a beam line that directs the particle beam from a particle source to a source output on a rotating gantry—each a time consuming process.

SUMMARY

Applicant has determined that it is advantageous to modulate the energy of a particle beam without changing the source particle energy or magnetic fields in the beamline. The energy modulation occurs, instead, with an external energy modulating device (EMD) disposed between the particle source output and the subject to deliver a dose to the target volume and allow for quicker energy modulation than would be possible in the beamline or at the source. Moreover, the energy modulation may be effectively increased or decreased as a function of gantry angle. The system and method embodiments described herein reduce or eliminate uncertainty in the relative biologic effectiveness (RBE) in a Bragg Peak region, due to the ability to rapidly place a Bragg peak within a target volume, and away from surrounding healthy tissue, resulting in smaller treatment volume margins necessary to effectively treat a target region. The systems and methods described herein result, in various embodiments, in decreased treatment time, a decrease in the integral dose delivered to a patient, decrease in treatment time, as well as an ability to maintain the integrity of the healthy tissue surrounding the target region.

In a first set of embodiments, a method includes receiving first data indicating a plurality of target volumes within a target region inside a subject for particle therapy. The first data indicates the plurality of target volumes relative to a particle beam outlet on a gantry for directing a particle beam from a particle beam outlet. The method also includes moving automatically one or more energy modulator components of an energy modulator device disposed between the particle beam outlet and the subject, to reduce an energy of the particle beam such that a Bragg Peak is delivered to at least one target volume of the plurality of target volumes. Still further, the method includes repeating the moving automatically as the particle beam outlet rotates with the gantry around the subject, without changing energy of the particle beam at the particle beam outlet, until every target volume is subjected to a Bragg Peak.

In a second set of embodiments, an energy modulator device includes a frame portion, two or more energy modulator components, a first and second attachment component, and an actuator. The frame portion defines an opening and is configured to be attached to a support with a particle beam outlet such that an axis of the particle beam outlet is directed through the opening. At least a first energy modulator component of the two or more energy modulator components is movable relative to at least a second energy modulator component of the two or more energy modulator components to variably block the opening. Each of the two or more energy modulating components is made of a material that reduces an energy of a particle therapy beam that passes through the energy modulator component. The first attachment component is configured for moveably connecting the first energy modulator component to the frame portion. The second attachment component is configured for connecting the second energy modulator component to the frame portion. The actuator is configured to move the first energy modulator component in response to a signal from a processor.

In other sets of embodiments, a computer-readable medium or system is configured to perform one or more steps of one or more of the above methods.

Still other aspects, features, and advantages are readily apparent from the following detailed description, simply by illustrating a number of particular embodiments and implementations, including the best mode contemplated for carrying out the invention. Other embodiments are also capable of other and different features and advantages, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

Embodiments are illustrated by way of example, and not by way of limitation, in the figures of the accompanying drawings in which like reference numerals refer to similar elements and in which.

DETAILED DESCRIPTION

Figure 1A:
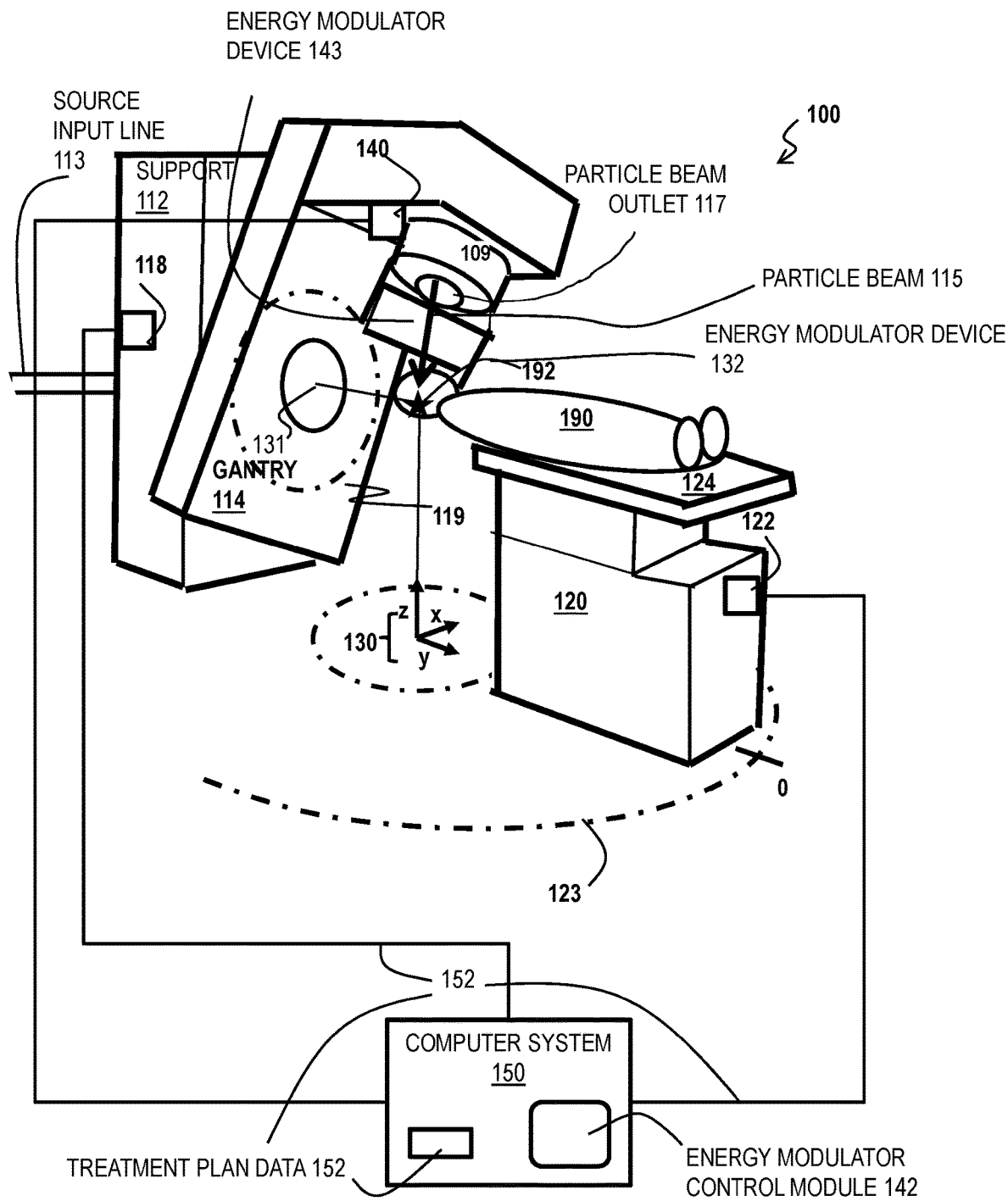
FIG. 1A is a block diagram that illustrates an example system for irradiation according to an embodiment.

A method and apparatus are described for particle beam therapy including modulating a particle beam with an energy modulator device. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Notwithstanding that the numerical ranges and parameters setting forth the broad scope are approximations, the numerical values set forth in specific examples are reported as precisely as possible. Any numerical value, however, inherently contains certain errors necessarily resulting from the standard deviation found in their respective testing measurements at the time of this writing. Furthermore, unless otherwise clear from the context, a numerical value presented herein has an implied precision given by the least significant digit. Thus a value 1.1 implies a value from 1.05 to 1.15. The term "about" is used to indicate a broader range centered on the given value, and unless otherwise clear from the context implies a broader range around the least significant digit, such as "about 1.1" implies a range from 1.0 to 1.2. If the least significant digit is unclear, then the term "about" implies a factor of two, e.g., "about X" implies a value in the range from 0.5x to 2x, for example, about 100 implies a value in a range from 50 to 200. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

Some embodiments of the invention are described below in the context of providing particle beam therapy, and controlling the particle beam energy with an external modulating device, wherein a particle beam energy may be decreased without adjusting the particle beam outlet in order to direct the particle beam to provide a more controllable relative biologic effectiveness (RBE) through a target volume of a target region. In many example embodiments, particle beam refers to a proton beam; however, the invention is not limited to this type of particle beam. In other embodiments, other high energy particles, including alpha rays (helium nuclei), beta rays (electrons), beta plus rays (positrons), and X-rays (photons), or carbon-ion may be used to deliver particle beam therapy to a subject. In some embodiments, passive scattering protons may be delivered, wherein a beam aperture system may shape the field shape at each gantry angle. In some embodiments, a scanning pencil beam is used in which scanning magnets point a pencil beam successively at different angles relative to an axis of the particle beam outlet. In some embodiments, energy modulation by way of an energy modulation device may be determined at each gantry angle to deliver a desired treatment depth of particle beams at the desired gantry angle, and depth. In other embodiments, multiple scanning angles may be delivered at each gantry angle.

1. Overview of Hardware Components

FIG. 1A is a block diagram that illustrates an example system 100 for irradiation, according to an embodiment. For purposes of illustration, a living subject 190 is depicted, but is not part of the system 100. As illustrated in FIG. 1A, a target region 192 is positioned within the subject 190. In an example embodiment, the target region 192 includes tumor cells. The system 100 includes a radiation source outlet port 109 having a particle beam outlet 117, which emits a particle beam 115, that penetrates to the target area 192. In some embodiments, the radiation is generated in a separate accelerator and fed into a gantry 114 along source input line 113 through a gantry support structure 112 and directed by one or more steering magnets in support 112 or gantry 114 or some combination to outlet port 109. In some embodiments, scanning magnets are included at the outlet port 109. Hereinafter the radiation source will be understood to mean the particle beam outlet 117 unless otherwise clear from the context. Combining the effects of multiple beams (their energies, intensities and shapes), the goal is to transmit high dose to the target region 192, and low dose to the tissue of the subject 190 outside the target region. During the operation of the system 100, the radiation source outlet port 109 rotates with gantry 114 around the support structure 112 and the subject 190 is positioned on a moveable couch 124 mounted on couch support 120, so that the beam is directed at the target region 192 from multiple directions. In the stationary global spatial coordinate system 130, the vertical dimension is indicated by a z axis, and the horizontal dimensions by an x axis perpendicular to the couch at a zero couch angle and a y axis oriented along the couch at zero couch angle as shown in FIG. 1A. This is related to the Digital Imaging and Communications in Medicine (DICOM) standard axes as given by Equation 1a through 1c.

$$X_{global} = X_{DICOM} \qquad (1a)$$

$$Y_{global} = -Z_{DICOM} \quad (1b)$$

$$Z_{global} = -Y_{DICOM} \quad (1c)$$

The gantry rotates an angle θ 119 in the x-z plane about an axis of rotation considered to occur at the origin 131 of the z axis and parallel to the y axis. The couch 124 can be moved at least vertically and rotated an angle φ 123 in the x-y plane around the z axis, and in some embodiments has six degrees of freedom consisting of three translational (x, y, z) and three rotational (yaw, pitch and roll) degrees of freedom.

As illustrated in FIG. 1A, a computer system 150 is provided to determine the particle energy, intensity (particle energy times number of particles) and, in some embodiments, the shape of the beam 115, from the particle beam outlet 117 for each of multiple beams at one or more gantry angles and one or more couch positions and orientations, according to a treatment plan. The computer system 150 also transmits the appropriate parts of the determined information: to a controller 118 for the gantry and radiation source; and to a controller 122 for couch 124. The information is transmitted over one or more wired or wireless communication lines 152.

The system 100 further includes an energy modulator device 143, which in various embodiments include one or more energy modulator components (not shown). The energy modulator device 143 may be mounted to the gantry 114, in one embodiment, or may be freely movable relative thereto. The energy modulator components may be movable relative to one another, wherein the energy modulator components move in a plane that transects an axis of the particle beam 115, such as a plane perpendicular to that axis. An axis of a particle beam refers to a center of scattered particles or a central pencil beam of a fan of scanning pencil beams. The energy modulator device moves with the gantry and the energy modulator components may move relative to the gantry and outlet 117 while the gantry 114 is in motion, and is used to adjust the energy of the particles in the particle beam 115. By way of the system embodiments described herein, adjustment of the particle beam 115 occurs between the particle beam outlet 117 and the subject 190. Moreover, in some embodiments described herein, the system provides adjustment of the particle beam 115 energy to distribute a Bragg Peak to a target volume of the target region 192 without changing the particle beam source upstream of outlet 117. In some embodiments, adjustment of the particle beam energy due to the position of the energy modulator components of device 143, occurs by way of a computer system 150 associated with the system 100.

The computer system 150 includes a control module 142 to generate signals to control the particle energy by way of the relative position of the energy modulator components, in some embodiments. In other embodiments, a controller 140 on the gantry 114 or a controller 118 on the support 112, or some combination, includes all or part of control module 142 to control the relative position of the energy modulator device 143 components relative to one another, or relative to the particle beam 115.

In some embodiments, a vibratory component is included in device 132 and is configured to vibrate the energy modulator device 143 components to spread a depth of the Bragg Peak in a subject 190. In some embodiments, the vibratory component comprises a motor or an acoustic speaker and is driven by the control module 142. The vibrator is attached to the energy modulator components to cause them to vibrate variably based on an electric signal from the controller 142 to the electromagnet to spread a depth of the particle beam Bragg Peak over at least a subset plurality of target volumes of a plurality of target volumes in the target region 192.

Figure 12:
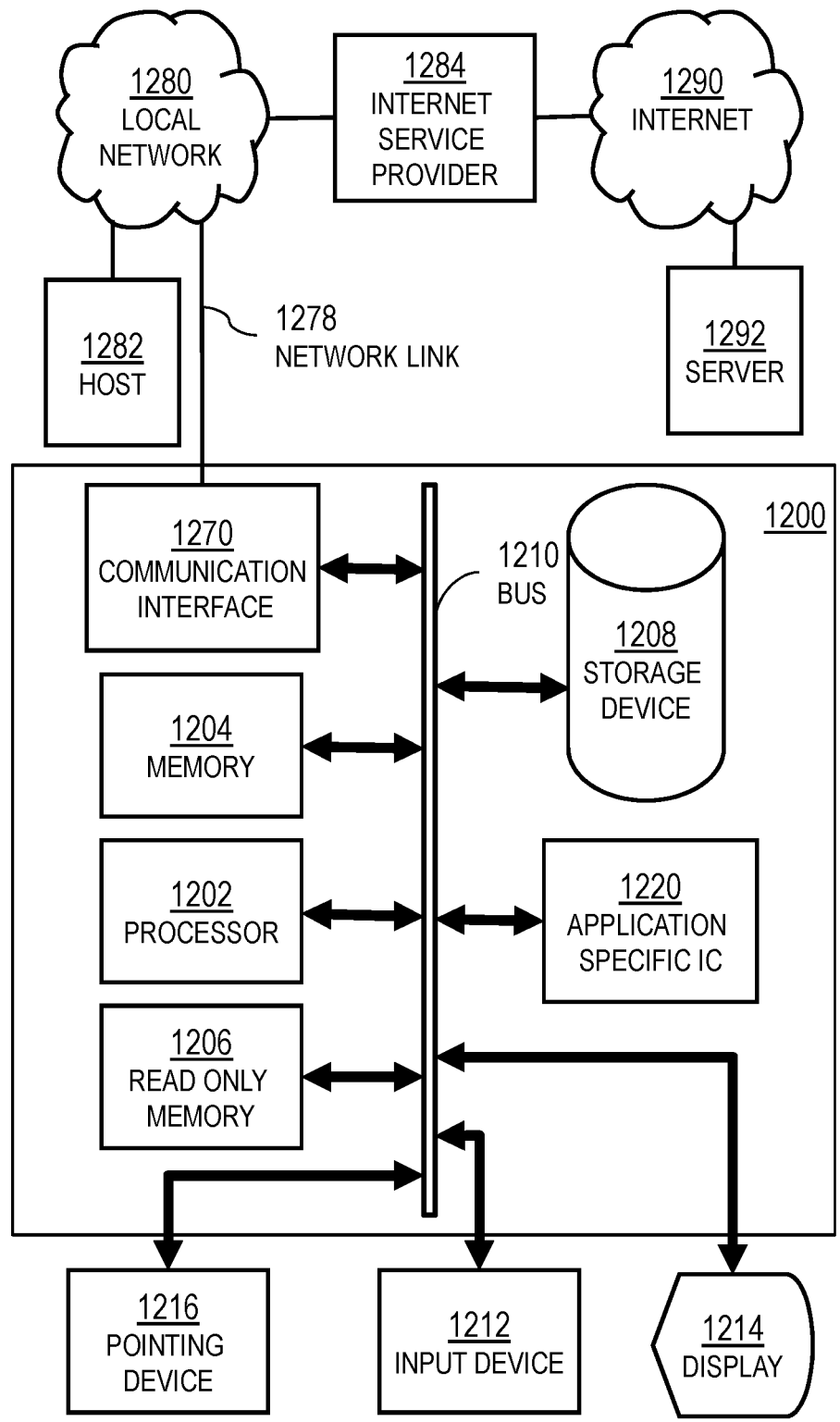
FIG. 12 is a block diagram that illustrates a computer system upon which an embodiment of the invention may be implemented.
Figure 13:
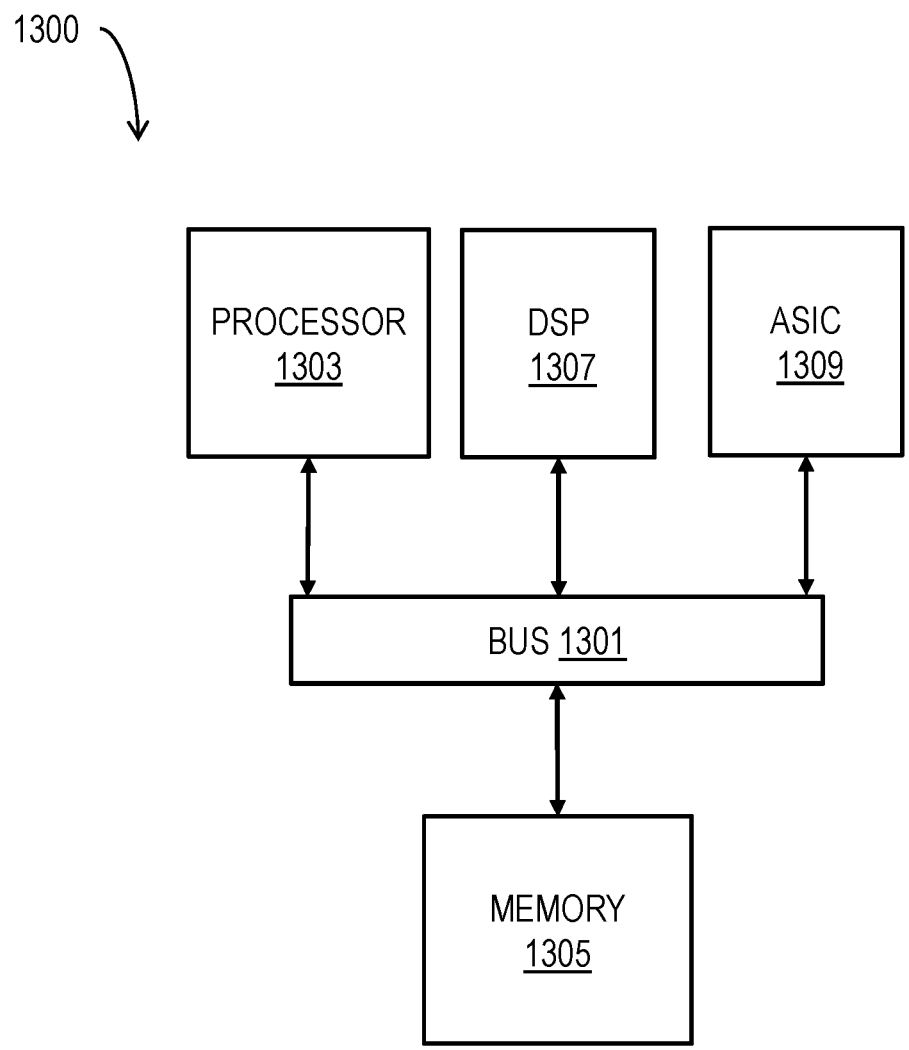
FIG. 13 illustrates a chip set upon which an embodiment of the invention may be implemented.

In various embodiments, the system 100 comprises one or more general purpose computer systems, as depicted in FIG. 12 or one or more chip sets as depicted in FIG. 13, and instructions to cause the computer or chip set to perform one or more steps of a method described below with reference to FIG. 10.

Although processes, equipment, and structures are depicted in FIG. 1A as integral blocks in a particular arrangement for purposes of illustration, in other embodiments one or more processes or data structures, or portions thereof, are arranged in a different manner, on the same or different hosts, in one or more databases, or are omitted, or one or more different processes or data structures are included on the same or different hosts. For example, all or part of module 142 may be performed by controller 118 for the gantry 114 and radiation source or by controller 122 for the couch 124, or by controller 140 for the energy modulator device, or some combination.

Figure 4:
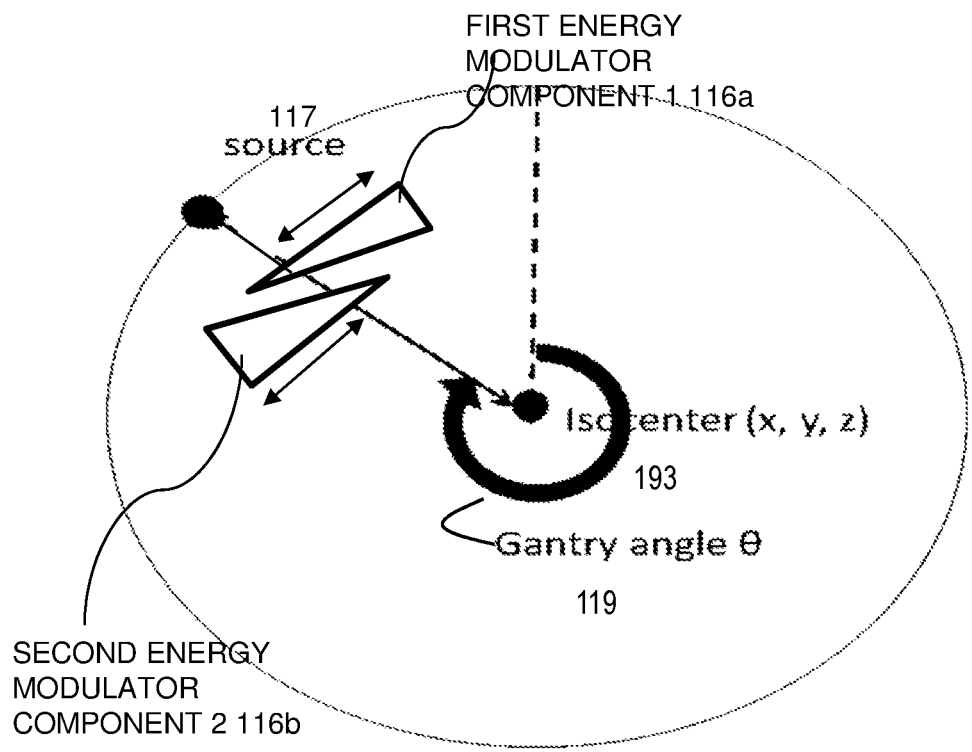
FIG. 4 is a block diagram that illustrates energy modulator components relative to an example gantry angle, according to an embodiment.

A treatment plan is prepared for treating a subject, such as a human or animal patient or a surrogate such as an inanimate phantom or control object, and includes treatment plan data 152 that indicates information about the subject placement on the couch 124, the height and orientation angle φ and other aspects of the couch position, the outer surface of the subject at φ=0 in global coordinates, the target region in global coordinates, including an outer surface of the target region and a central point, called the isocenter 193 (isocenter shown in FIG. 4). The isocenter 193 is near or inside the target region 192; and, is aligned with the axis of rotation of the gantry 114 and the axis of rotation of the couch 124. After treatment of the target region 192 in the neighborhood of the isocenter 193, the couch 124 can be moved horizontally and vertically or the gantry 114 rotated, or some combination, so that a different target region inside the subject 190 can be treated and a different point occupies the isocenter 193. In particular, however, during treatment, one or more of the energy modulator components may be automatically moved to reduce the energy of the particles in the beam 115 to deposit a Bragg Peak within a target volume within the target region (e.g., target volume 198 shown in FIGS. 6-7). The position of the couch 123, the gantry 114, the particle beam outlet 117, and the energy of the particle beam 115, may be determined as part of a treatment plan data 152, and controlled by way of computer system 150, specifically by way of the energy modulator control module 142, either before, during, or after treatment.

Figure 1B:
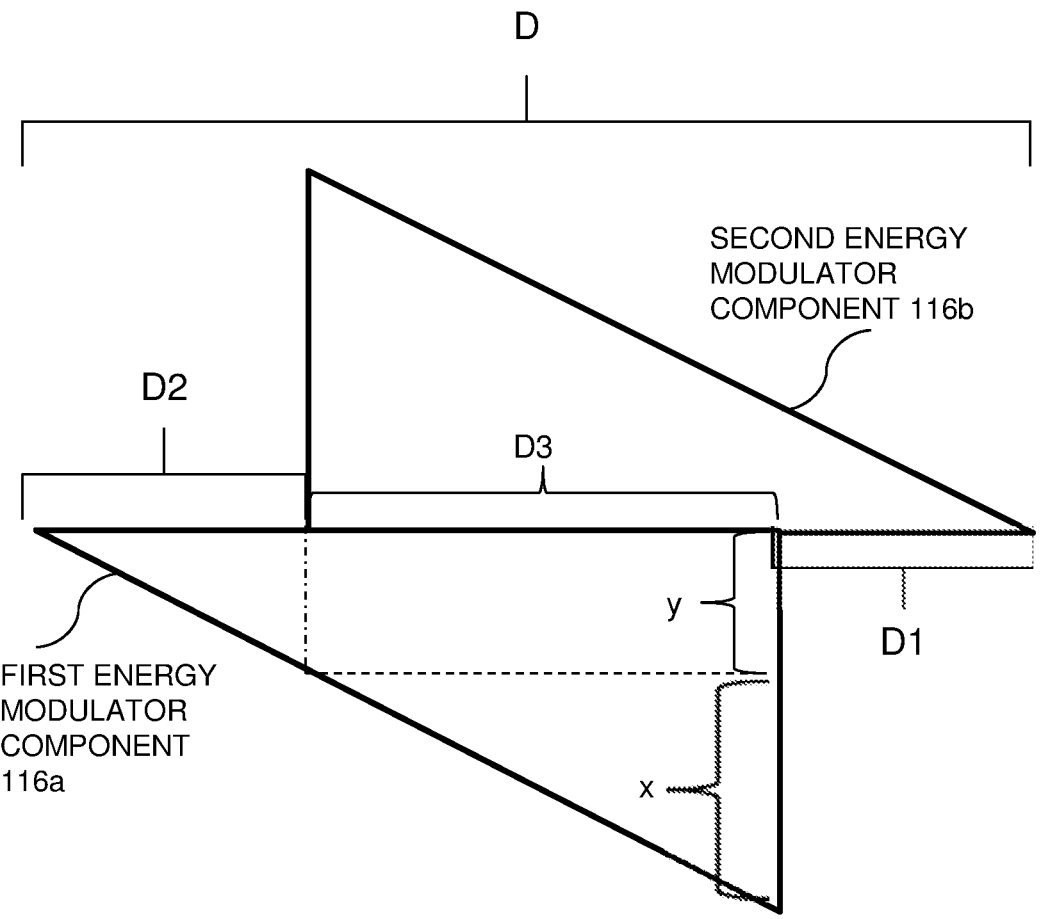
FIGS. 1B and 1C each is a block diagram that illustrates example energy modulator components, according to various embodiments.
Figure 1C:
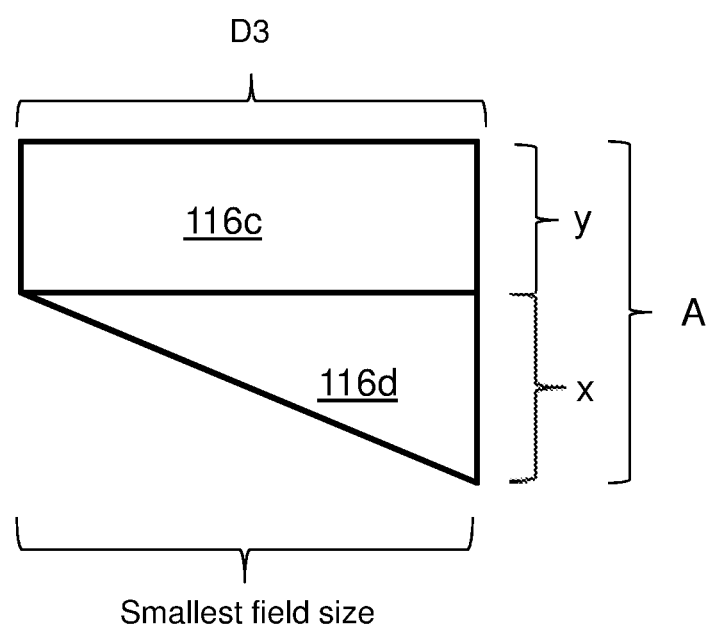

FIGS. 1B and 1C each is a block diagram that illustrates example energy modulator components, according to various embodiments. Each component is made of a material that serves to slow the particles in the particle beam and thus reduce the particle energy. The two components can be made of the same material or different materials. In other embodiments, additional components are added, of the same or different materials. The components described herein include, in some embodiments, low density materials, i.e., materials with a low Z (atomic number). High density materials are also used to form the components, in some embodiments, wherein the higher density materials cause the particle beam to scatter and creates larger spots with higher activation. In an embodiment, the material of a component includes polyethylene, or lucite, or a combination thereof.

FIG. 1B illustrates a first energy modulator component 116a and a second energy modulator component 116b, disposed relative to one another to provide a distance (D) of range of movement of the energy modulators 116a, 116b, and to demonstrate, for example, overlap of the first energy modulator component 116a (moved a distance D1 from a right edge of the figure), and overlap of the second energy modulator (moved a distance D2 from a left edge of the figure), wherein a target field size (D3 between D2 and D1) is established where a beam passes through both components. A scattered or scanned pencil particle beam is not designed to pass outside the target field, so the maximum energy loss is accomplished when there is the most overlap in the field size, and the total thickness traversed by a beam is the same within the field size distance D3.

FIG. 1C illustrates an example of a target field size for irradiation of a first and second energy modulator 116c, 116d, to provide a distribution of a dose of treatment to a target region that is not constant. Thus, particle beams traversing different parts in this field size will penetrate to different depths before depositing the Bragg Peak. In an embodiment, a preferred field size may include a 6 cm by 30 cm area, wherein the field will be flat, and the beam will be maintained through that portion of the components. In some embodiments, the energy of the particle beam for each gantry angle will be generally maintained at all positions for that angle. Increasing angles a or b in FIG. 1D would change the energy of the particle beam at a faster rate, and the thickness of the energy modulator device will increase and/or decrease more quickly as the components move relative to one another with larger a or b angles.

Figure 1D:
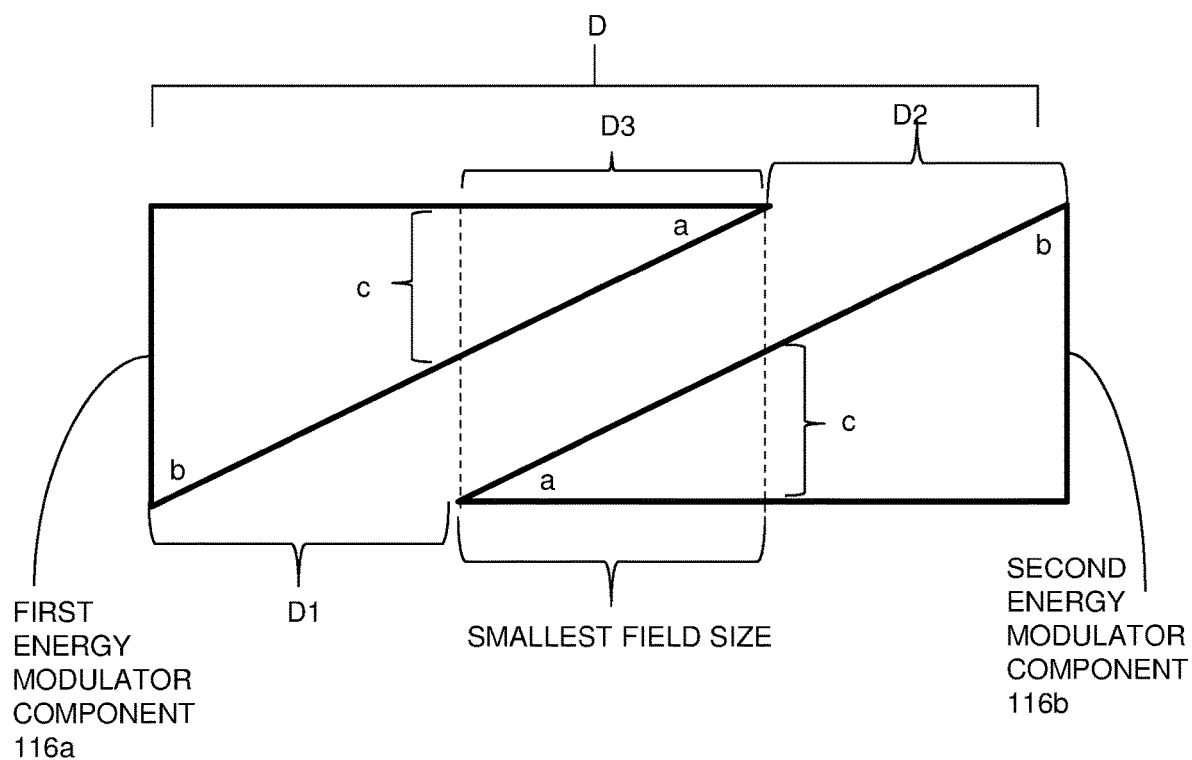
FIG. 1D is a block diagram that illustrates an example overlap of components relative to a smallest preferred field size, according to an embodiment.

FIG. 1D is a block diagram that illustrates an example overlap of components 116A, 116B relative to a smallest preferred field size (D3), according to an embodiment. In FIG. 1D the thickness of material traversed is constant over the smallest field size (D3). As shown in FIG. 1D, in some embodiments, the components will create a field providing a generally consistent thickness over the target area to distribute the particle beam over the target area with a generally consistent depth.

Figure 2:
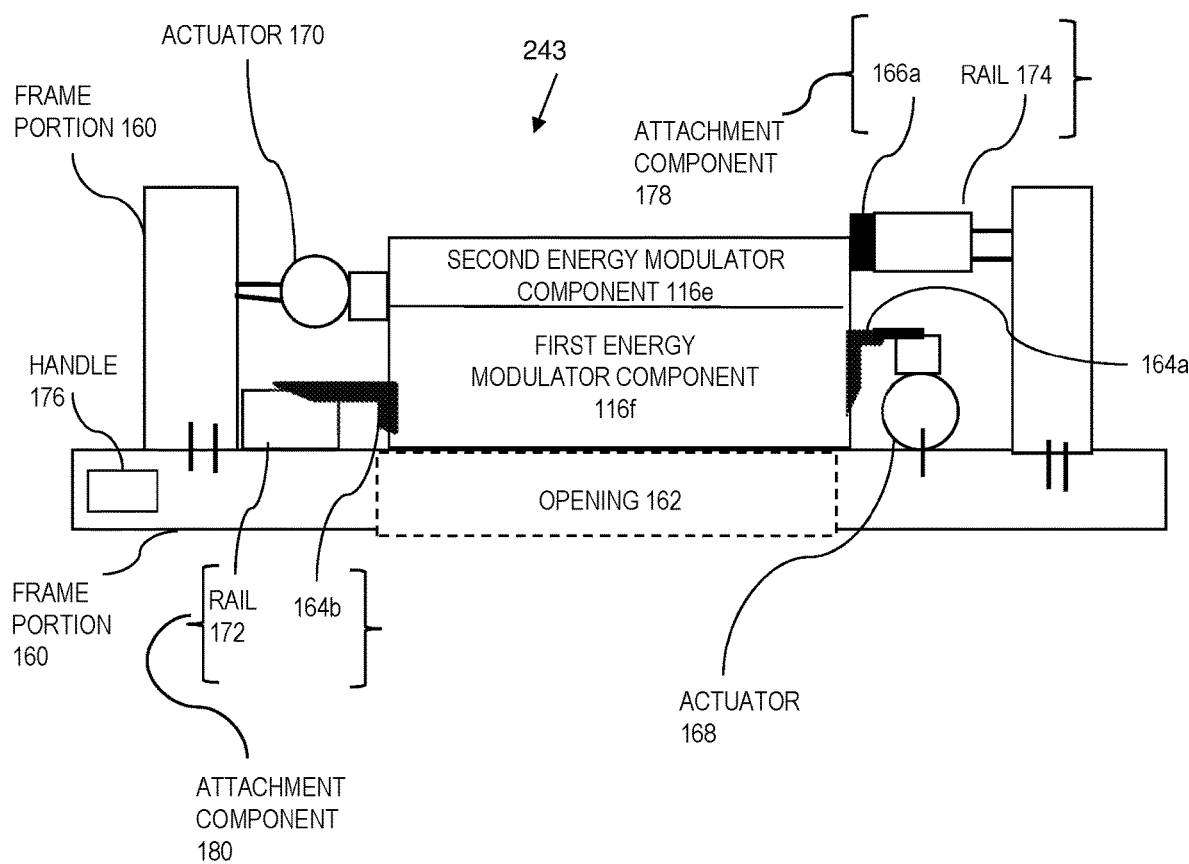
FIG. 2 is a block diagram that illustrates an end view of an energy modulator device, according to an embodiment.

FIG. 2 is a block diagram that illustrates an end view of an energy modulator device 243, according to an embodiment. The device 243 includes a frame portion 160 defining an opening 162 with two or more energy modulator components 116e, 116f, of which at least one is moveable relative to the frame portion 160. The frame portion 160 is constructed so as to fit on the gantry or other support of the particle beam outlet so that the beam 115 passes through the opening 162. In some illustrated embodiments, for example in FIGS. 1A-1D, the energy modulators 116e, 116f are shown as right triangular shaped wedges; however, this is not intended to be limiting. The energy modulators 116e, 116f may include other shapes, or may include isosceles, obtuse, equilateral, scalene, or acute triangular shaped wedges, for example. At least a first energy modulator component of the two or more energy modulator components 116e, 116f is movable relative to at least a second energy modulator component of the two or more energy modulator components 116e, 116f to reduce an energy of a particle therapy beam that passes through the opening and through at least one energy modulator component 116e, 116f.

In the embodiment shown in FIG. 2 a first attachment component 178 and a second attachment component 180 are shown. An attachment component may include both a rail and a bracket (as shown herein), either a rail or a bracket, or neither a rail nor a bracket in various embodiments. In the embodiment shown in FIG. 2, each attachment component includes a rail and a bracket. For example, as shown in FIG. 2, a first attachment component 178 comprises a bracket 166a and a rail 174 to moveably connect the first energy modulator 116e to the frame portion 160. A second attachment component 180 comprises a bracket 164b and a rail 172 to moveably connect the second energy modulator 116f to the frame portion 160. In this manner, the energy modulator components 116e, 116f may be slidable in the frame portion 160 within the opening 162 relative to one another, in the illustrated embodiment.

At least one actuator 170 motivates energy modulator component 116e to move along rail 174. In the illustrated embodiment, a second actuator 168 motivates energy modulator component 116f to move along rail 172. In some embodiments, the movement of energy modulator components 116e, 116f relative to each other is accomplished with only one actuator moving one component or one actuator moving both components. For example, a screw drive or stepping motor is used as actuator 170 or 168 or both. In some embodiments, the frame portion 160 includes a handle 176 to facilitate disposing the frame portion 160 on the gantry 114 or other support so that the opening 162 aligns with an axis of the beam 115 from the beam outlet 117.

A processor including an energy modulator control module 142 provides analog or digital signals to the actuator(s) 168, 170, for automatic movement of the energy modulator component(s) 116f, 116e, respectively, transverse or perpendicular to the beam 115 (shown in FIG. 1A), and in some embodiments communicate via the controller 140.

Figure 3:
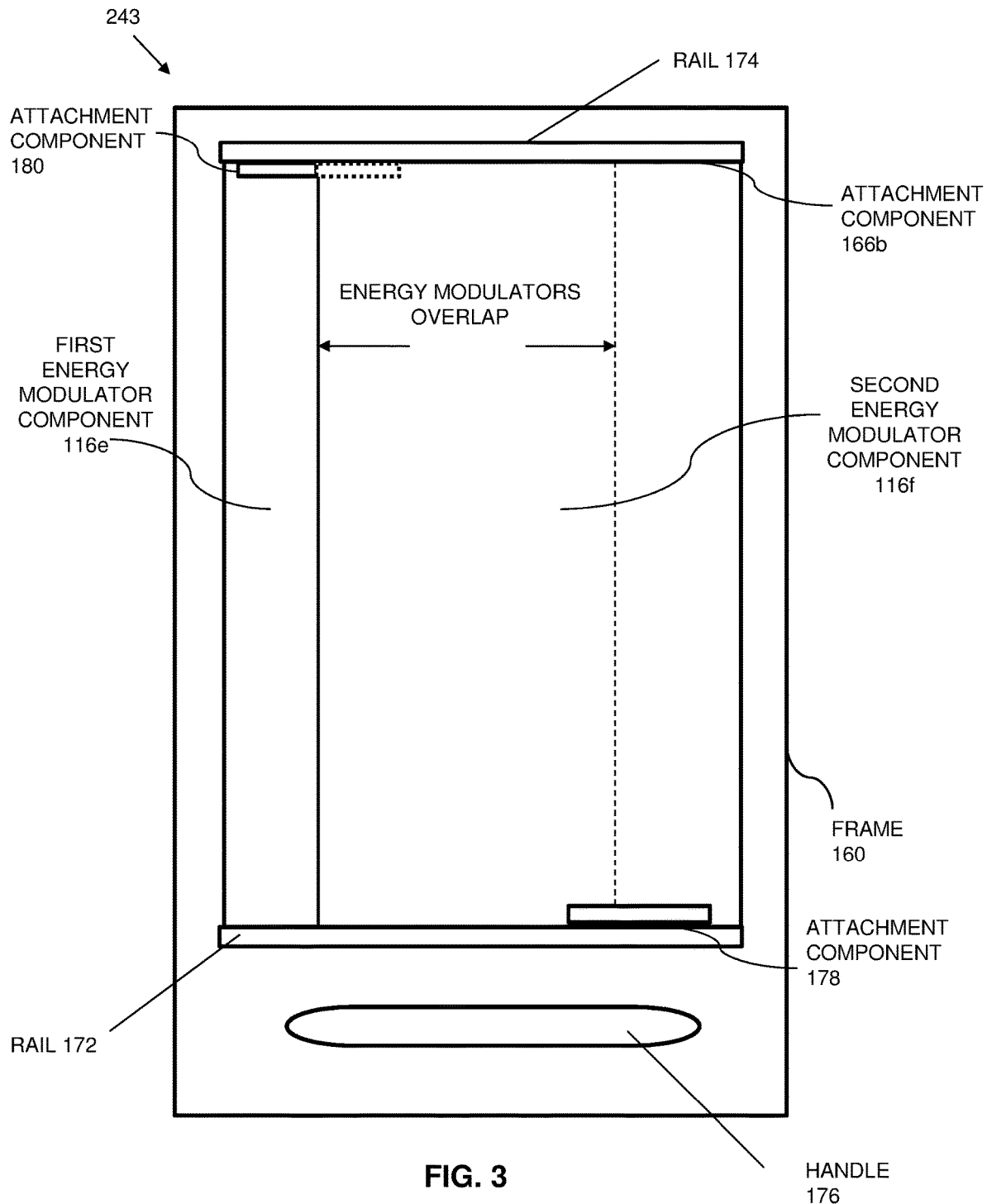
FIG. 3 is a block diagram that illustrates top plan view of an energy modulator device, according to an embodiment.

FIG. 3 provides a top plan view of an embodiment of the energy modulator device 243, whereby the frame portion 160 surrounding the device 243 is shown having at least the first rail 172 and the bracket 164b, together forming an attachment component 180, for movably connecting a first energy modulator 116f, and the second rail 174 and the bracket 166a, together forming an attachment component 178, for movably connecting the second energy modulator 116e. Actuator 170 moves the second energy modulator 116e, and actuator 168 moves first energy modulator 116f.

Figure 5:
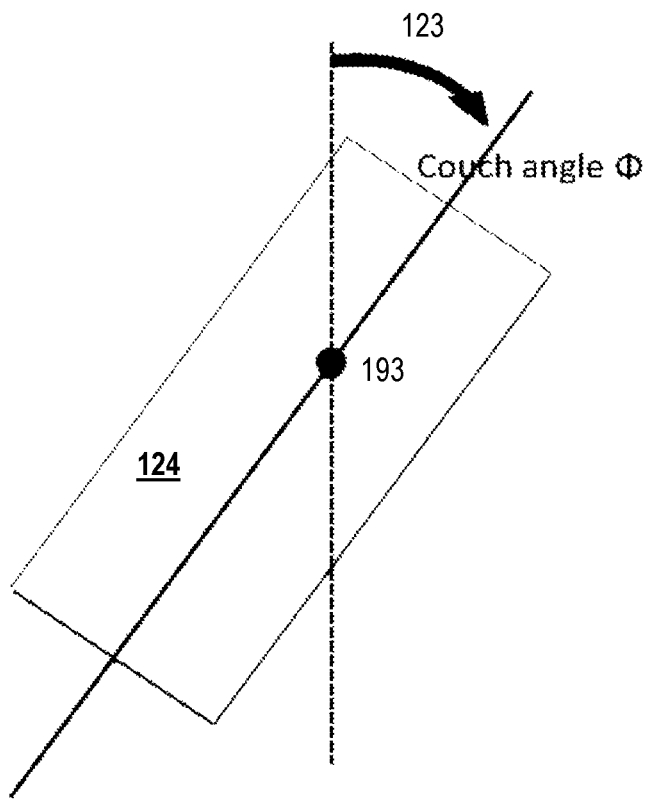
FIG. 5 is a block diagram that illustrates example couch angle, manipulated according to an embodiment.

FIG. 4 is a block diagram that illustrates energy modulator components relative to an example gantry angle, according to an embodiment. FIG. 4 depicts the gantry angle θ, measured in this example clockwise relative to the radiation source pointing straight down (−z direction) in the z-x plane looking back along the −y direction, and provides a visual representation of the placement of the energy modulator components 116a, 116b relative to the particle beam outlet 117 and the isocenter 193. FIG. 5 is a block diagram that illustrates example couch angle φ, manipulated according to an embodiment. FIG. 5 depicts the horizontal surface of the couch 124 in the x-y plane and the couch angle φ, measured in this example clockwise, looking in the −z direction, from the y axis that is parallel to the axis of rotation of the gantry.

Figure 6:
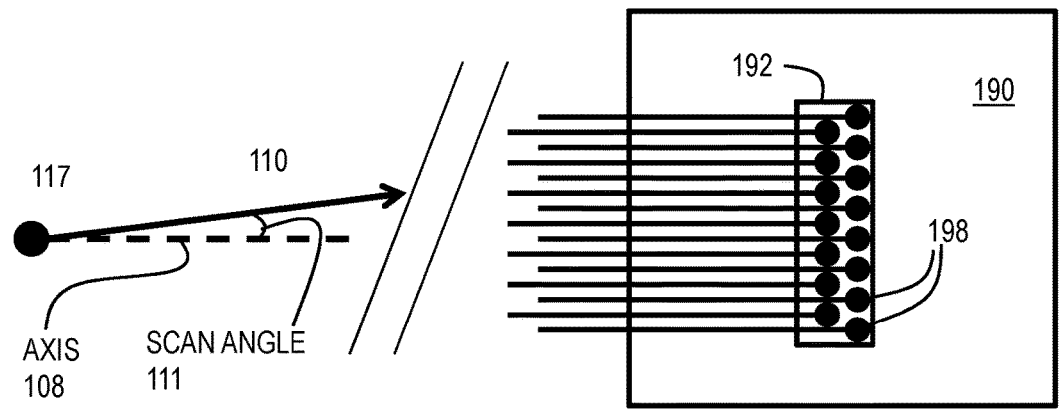
FIG. 6 is a block diagram that illustrates an example scanning pencil beam radiation particle source, used in many modern particle beam sources, according to some embodiments.

FIG. 6 is a block diagram that illustrates an example particle beam outlet 117, which in the illustrated embodiment includes a scanning pencil beam radiation source. At any instant, only a thin beam called a pencil beam (also called a beamlet) is emitted from the outlet 117. Scanning components (e.g., magnets or optics, not shown) are used to point the pencil beam through any of a variety of small scan angles 111 around a beam axis 108 at the center of a fan of such beamlets. The scanning is accomplished over a short time, completing the fan in a time on the order of milliseconds to seconds. Each beamlet 110 penetrates the skin of a subject 190 to a target region 192 where the energy is largely absorbed at one subregion 198 called a target volume, also called a "spot" hereinafter for convenience. As the pencil beam is scanned over multiple angles 111, the energy is primarily absorbed at multiple target volumes 198 at one depth within the subject.

By using a pencil beam of different initial particle energy, such as imposed by relative movement of the two or more energy modulator components, the beam energy is absorbed in a target volume 198 at a different depth. In a short time, multiple target volumes 198 that span the entire target region 192 are radiated. For example, in some experimental embodiments, the distance from the outlet port is about 230 cm, beamlet width is between 6 mm to 12 mm in air; and, it takes a few milliseconds to deliver one spot, a few seconds for one energy layer, and a few minutes for one scan. The beam width depends on the energy of the beam, and can also depend on other factors, such as whether a collimator is used, for example. For a scanning pencil beam, the beamlets are nearly parallel in the vicinity of the target region 192 and some beam paths are reused to target spots at different depths. Consequently, the positioning of the energy modulator device 143 between the outlet 117 and the subject 190 is critical in order to adjust the energy of beam 115, and in many cases, to decrease the beam 115 energy to effect deposition of a Bragg Peak at a target volume at a different depth within the target region 192, sparing the healthy surrounding tissue.

Figure 7:
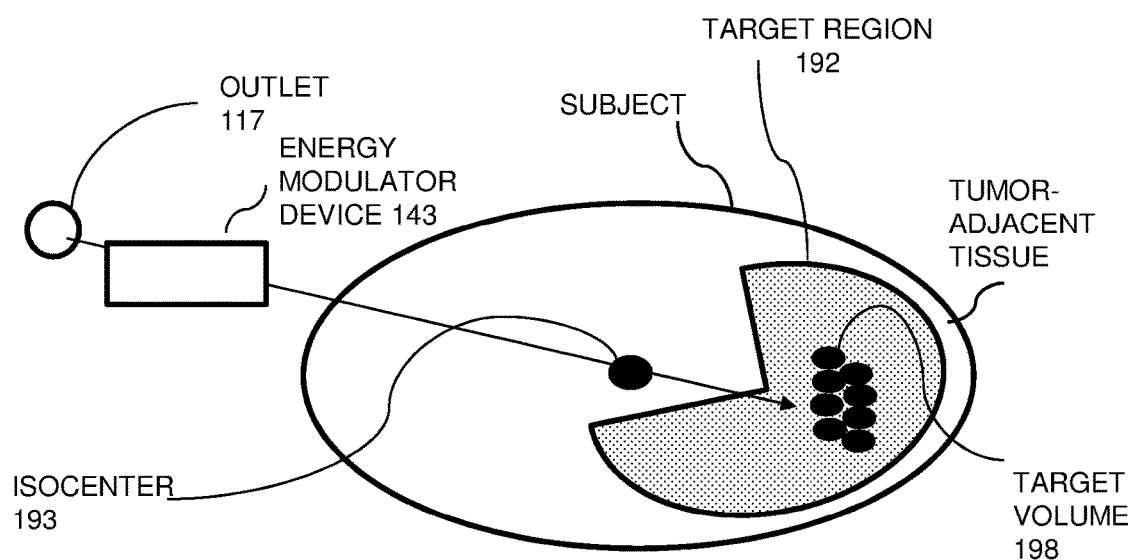
FIG. 7 is a block diagram that illustrates an example position of an energy modulator device relative to a target volume according to some embodiments.

FIG. 7 is a block diagram that illustrates example positioning of an energy modulator device such as 143 or 243 relative to a target volume, according to one embodiment. FIG. 7 includes an outlet 117 from which a particle beam 115 is delivered, and an energy modulator device 143 (such as device 243), positioned between the outlet 117 and the subject 190, so as to deliver the particle beam 115 to a target volume 198 of the target region 192 according to one embodiment.

Figure 8:
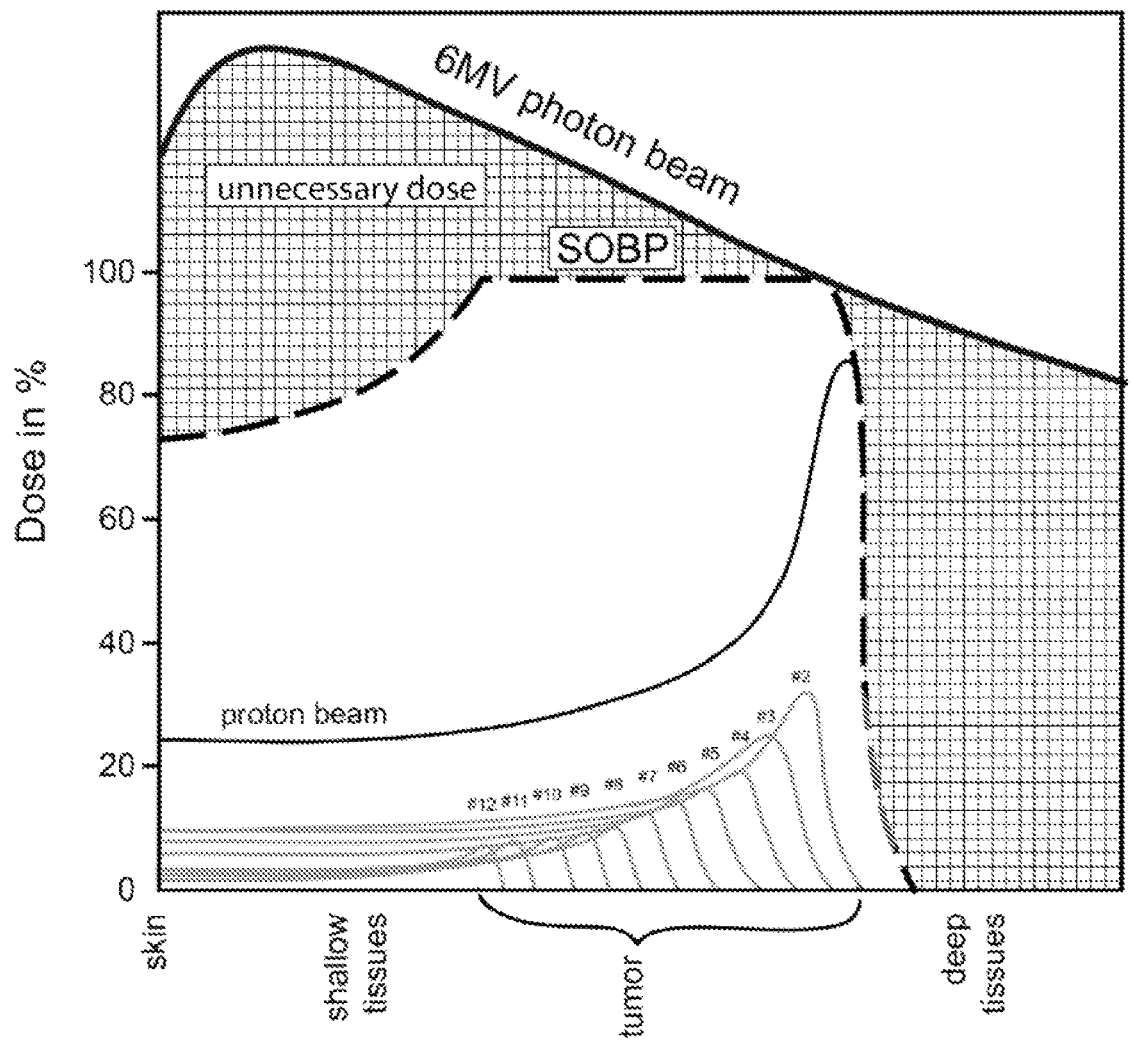
FIG. 8 is a graph that illustrates an example spread out Bragg Peak (SOBP) that can be achieved, according to some embodiments.

As a single Bragg Peak covers very little depth of tumor, traditional particle beams are clinically utilized by stacking Bragg Peaks from the highest energy (deepest deposition) to lowest energy (shallowest) to create the spread out Bragg Peak (SOBP). FIG. 8 is a graph that illustrates an example spread out Bragg Peak (SOBP) that can be achieved, according to some embodiments FIG. 8 shows energy deposition by multiple different initial energy particle beams traversing the same path into a subject and target region, according to previous approaches. In some embodiments, the SOBP is placed in a target volume of a target region as a treatment is delivered. This is designed to occur without changing the intensity of the particle beam or the energy of the proton at the beam source 116, but instead by modulating the energy by way of the energy modulator device 143 (such as device 243) as described in embodiments herein. The modulation occurs by manipulating the energy modulator components 116a, 116b relative to one another to reduce the energy of the particle beam 115 and control the deposition of the Bragg Peak in the target volume region 192. In one specific embodiment, a system is configured to maintain the SOBP within the treatment volume 198 as the gantry 114 rotates around a subject during treatment, focusing the radiation into the tumor tissue and avoiding delivery of particle beams 115 to surrounding healthy, tumor-adjacent tissue.

Figure 11A:
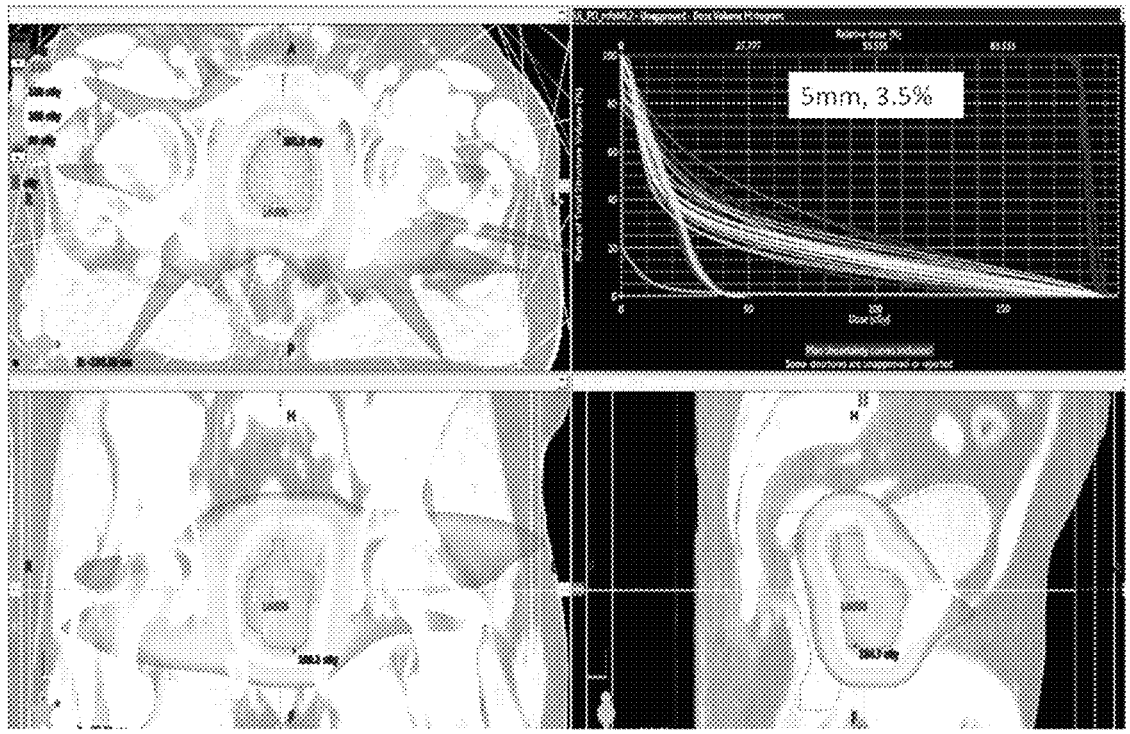
FIG. 11A is an image that illustrates example treatment of a prostate tumor, according to an embodiment.
Figure 11B:
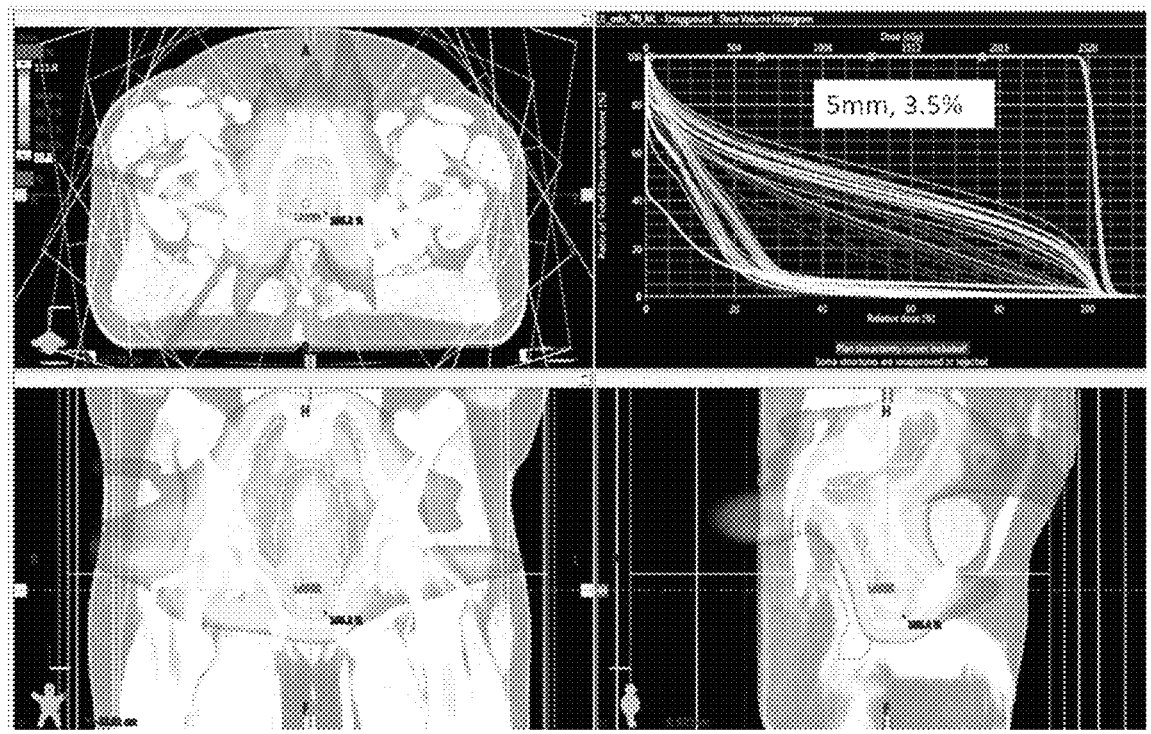
FIG. 11B is an image that illustrates example treatment of a prostate tumor and nodes according to an embodiment.
Figure 11C:
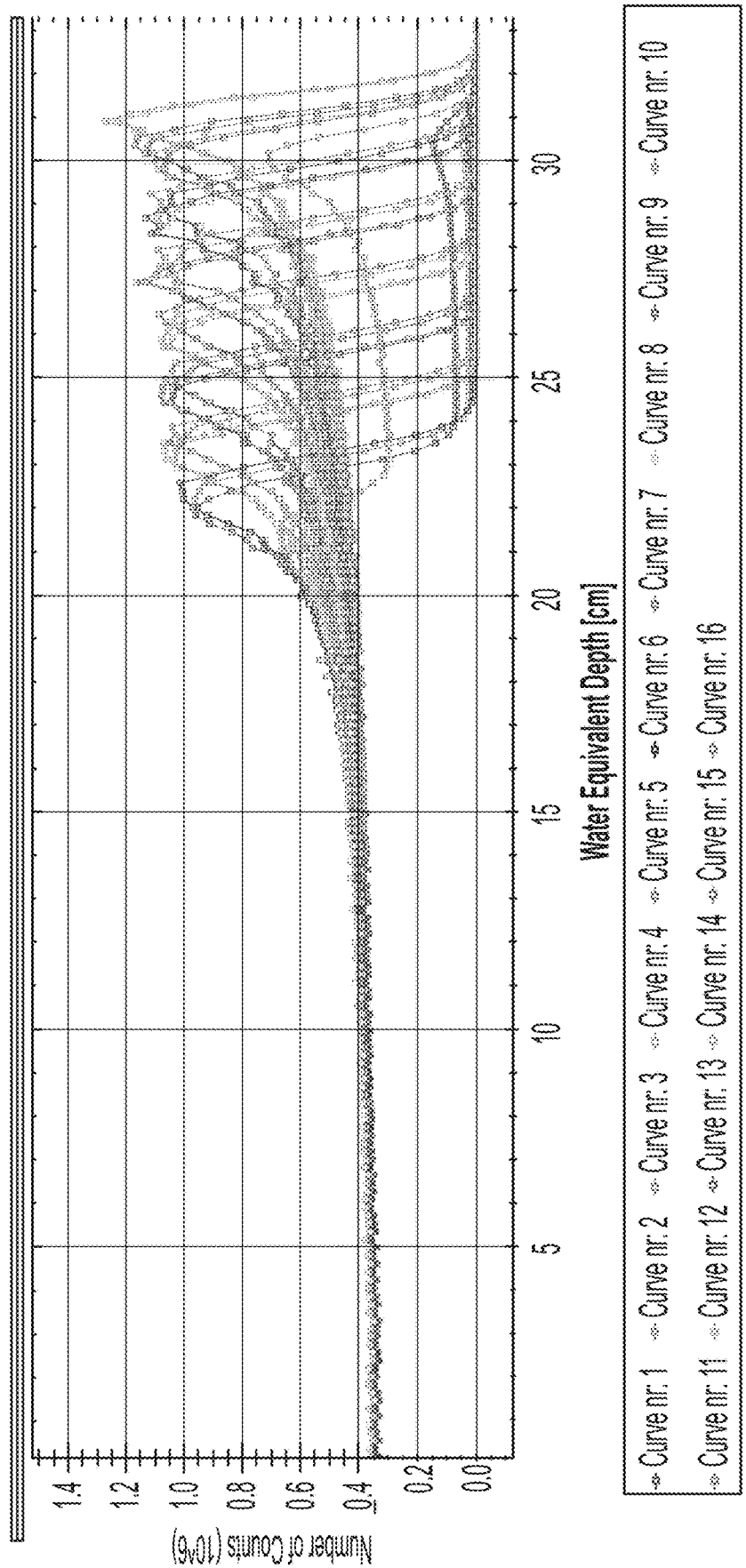
FIG. 11C is a graph that illustrates sample results of an example treatments of a target region using an energy modulator device according to an embodiment.
Figure 11D:
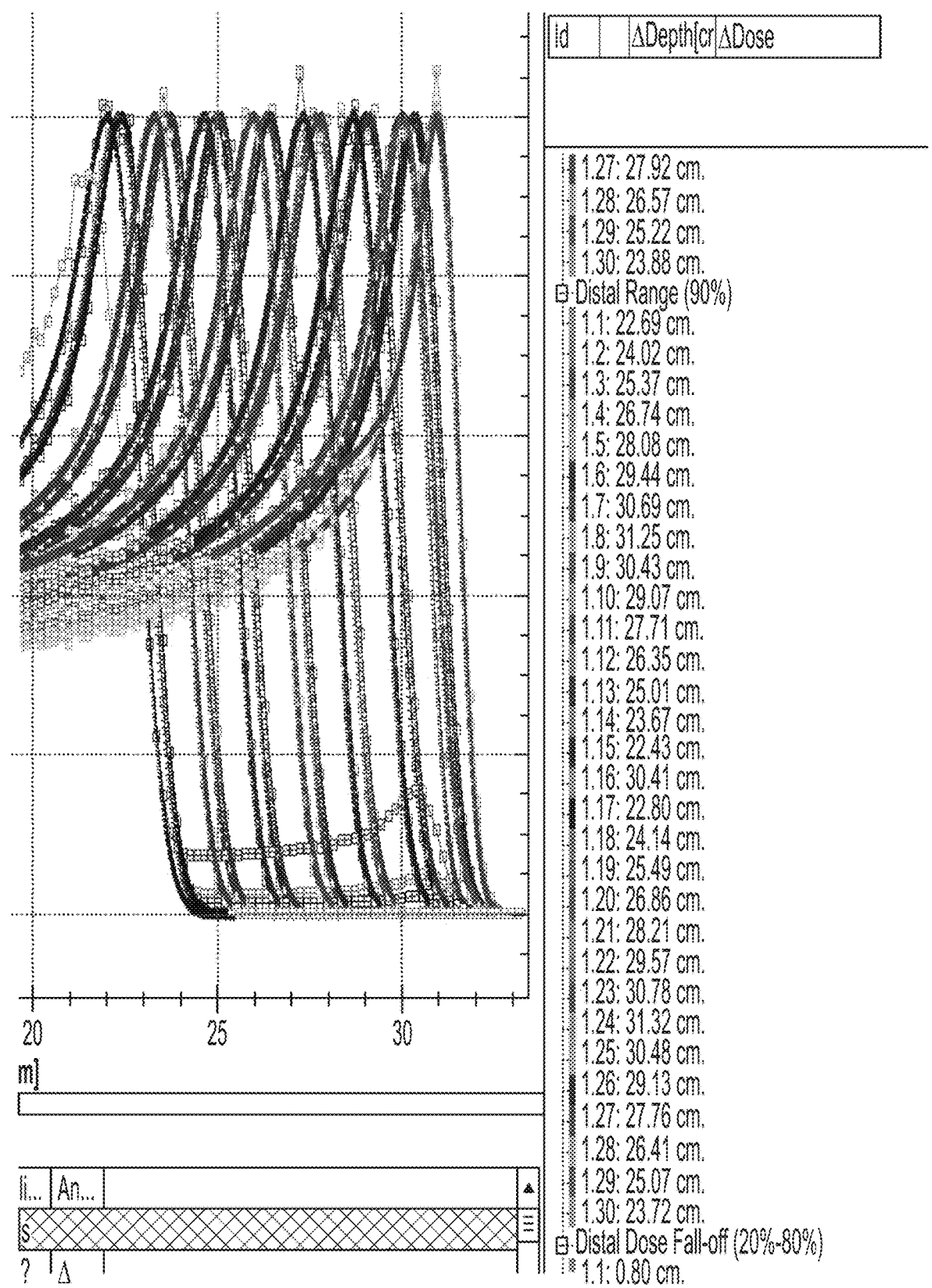
FIG. 11D is a graph that illustrates sample results of an example treatments of a target region using an energy modulator device according to an embodiment.

In other embodiments, the thickness of the energy modulator device by moving the energy modulator components relative to one another, may be changed to simulate the thickness of ⅔ of the target area within 2 to 3 degrees of a gantry rotation. For example, if the gantry rotates at one revolution per minute, the rotation time for 3 degrees is 0.5 seconds. Therefore, the thickness of the components must change approximately 5 centimeters in 0.5 seconds. This depends on the target area size in the beam direction, which will dictate the energy range needed. In one example, shown in the graphs of FIGS. 11C-11D, showing movement of 8.63 cm in 4 seconds, wherein the frame rate was 250 mHz. Therefore, a movement of 1.1 cm can occur in 0.5 seconds, in one example. The speed is increasable by slowing the gantry or by increasing the speed of the actuator(s).

In some embodiments, in order to attain a SOBP is a short time relative to the gantry motion, a high frequency vibration is applied to the energy modulator components. For example, an energy modulator component displacement in a range from about 1 to 10 millimeters is applied in a frequency range from about 1 Hz to about 1 kilohertz.

Figure 9:
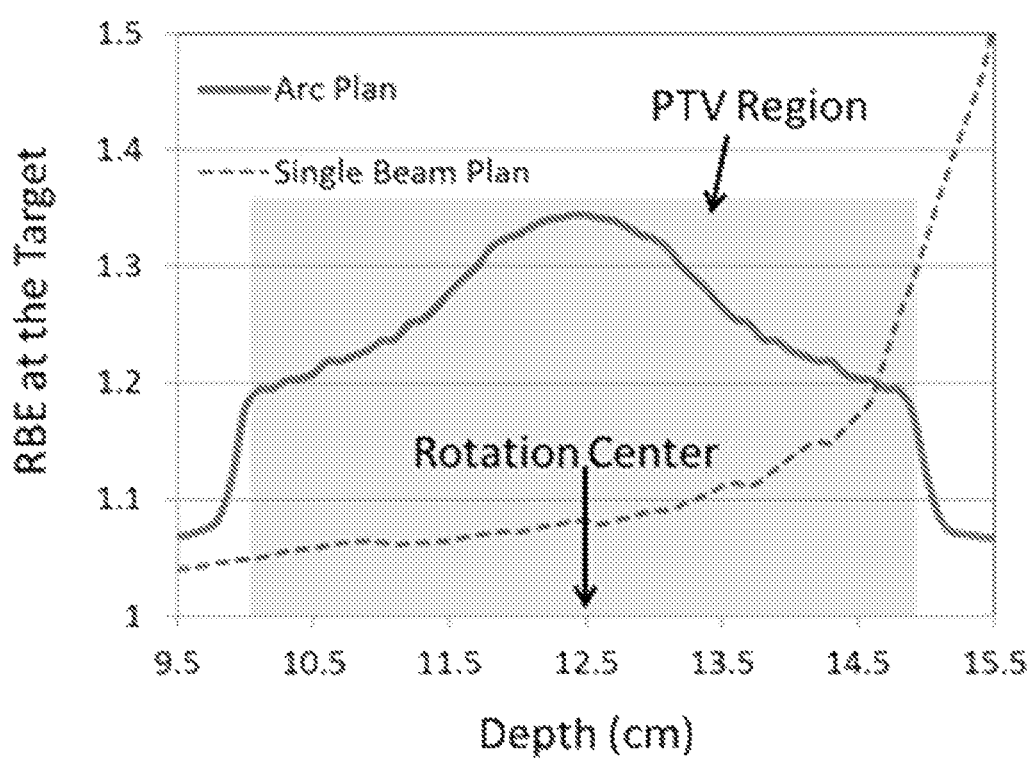
FIG. 9 is a graph that illustrates an example PTV region, and differences between arc plan and single beam plan, showing RBE at the target, according to an embodiment.

The use of an energy modulator device improves dose delivery in a subject. FIG. 9 is a graph that illustrates an example planning target volume (PTV) region, and differences between arc plan and single beam plan, showing relative biological effectiveness (RBE) at the target, according to an embodiment. Planning target volume is the gross tumor volume plus a clinical margin used to create the clinical target volume (CTV), plus a margin of error. FIG. 9 shows RBE at target region 192 on the y-axis as compared to depth of treatment in the tissue, provided on the x-axis. Differences between an arc plan treatment and a single beam plan treatment in the PTV region is shown by graphical representation, wherein the PTV region achieves a greater RBE at the target near the rotation center, than what is achievable with a single beam plan. These multiple beam results are due in part to the energy modulator device 143, 243, which decreases the energy of the beam 115, placing the Bragg peak within a target volume 198, within a PTV region, and also due to rotation of the beam outlet 117 and beam source relative to the subject being treated. Furthermore, a decreased dose of radiation can be used, and will more effectively radiate a target region due to the placement of the Bragg Peak in the PTV region as shown.

2. Overview of Method

Figure 10:
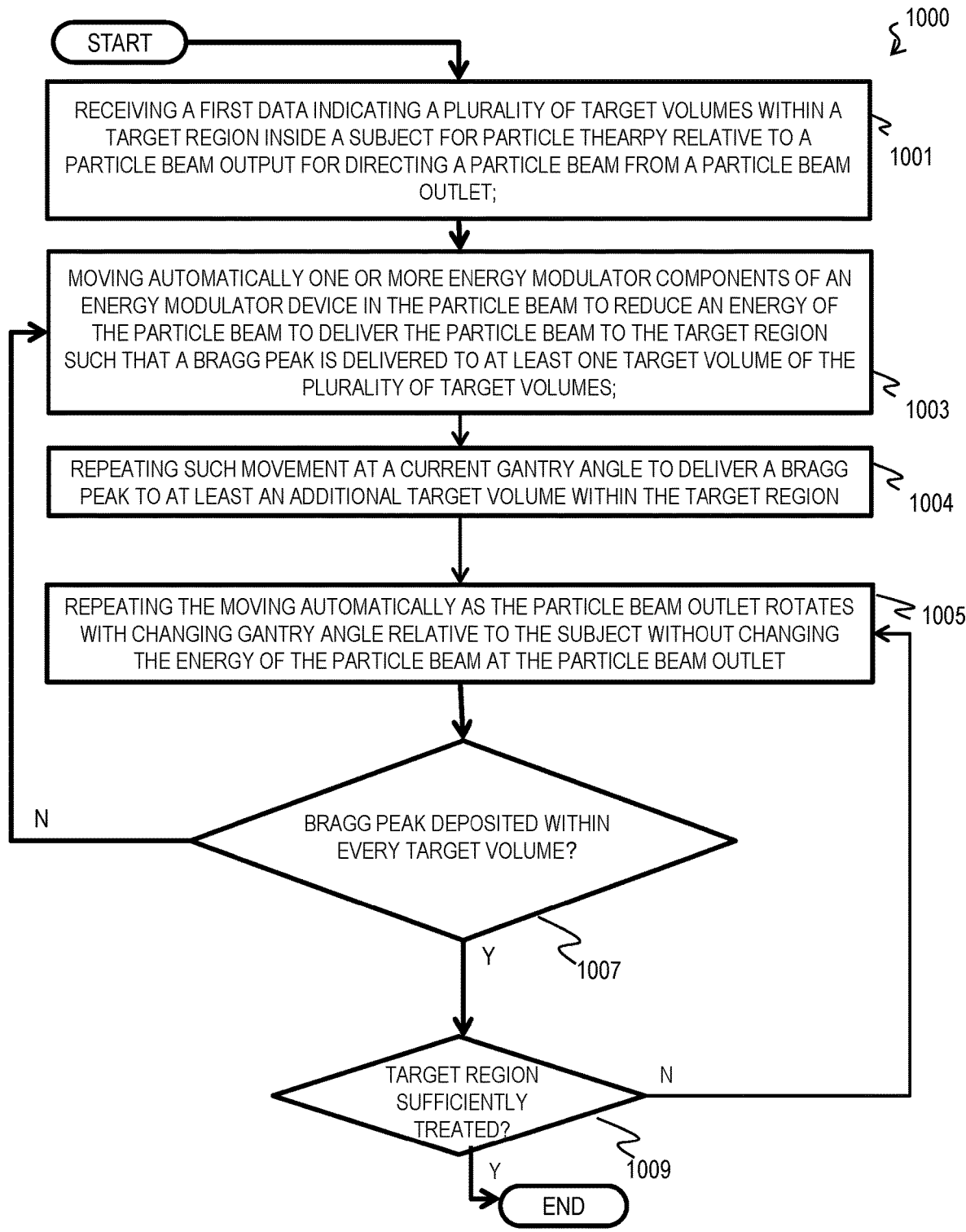
FIG. 10 is a flow diagram that illustrates an example method to provide particle therapy, according to an embodiment.

FIG. 10 is a flow diagram that illustrates an example method 1000 for providing beam therapy to a subject, according to an embodiment. In step 1001 first data is received, which indicates a plurality of target volumes within a target region inside the subject for therapy, relative to a particle beam outlet 117 configured for directing a particle beam. The method 1000 further includes step 1003 for moving, automatically, one or more energy modulator components of an energy modulator device in the path of the particle beam to reduce an energy of the particle beam. Thus the particle beam is delivered to the target region, such that a Bragg Peak is delivered to at least one target volume of the plurality of target volumes. In step 1004, before the gantry has moved, or moved appreciably, the components are moved again to place the Bragg Peak at a different depth, and thus produce something akin to a spread out Bragg Peak (SOBP). The method 1000 further includes in step 1005 repeating steps 1003 and 1004 automatically as the particle beam outlet rotates with the gantry around the subject, all without changing energy of the particle beam at the particle beam outlet. This repeating is done until every target volume is subjected to a Bragg Peak or SOBP. Following the repeating step 1005, and/or following the moving automatically step 1003, the method 1000 includes determining 1007 whether a Bragg Peak was deposited within every target volume. If the Bragg Peak was not deposited within every target volume, the method 1000 includes repeating the moving automatically step 1003, following adjustment of the energy modulator device, or at least one of its energy modulator components, to effectively deposit the Bragg Peak within the remaining target volume. The method 1000 further includes, if the Bragg Peak was deposited within every target volume in step 1007, determining 1009 whether the target region was sufficiently treated. If the target region was sufficiently treated, e.g., the difference between the dose deposited and target therapeutic dose, then the method 1000 has been completed. If the target region was not sufficiently treated, the method 1000 includes repeating the repeating 1005 the moving step.

3. Example Embodiments

Example embodiments include demonstrating the techniques for proton beam therapy for a prostate tumor. FIG. 11A is an image that illustrates example treatment of a prostate tumor, according to an embodiment. FIG. 11B is an image that illustrates example treatment of a prostate tumor and nodes according to an embodiment. The different gray shades represent different isodose lines as indicated by the grayscale bar. The first volume (95% isodose) shown by a first grayscale line 1101 includes the target. The idea of these was to show that a treatment plan using this concept of energy modulation can produce clinically feasible plans. The spread of lines of each grayscale in the top right corner are the robustness of the isodose lines. The patient CT is shifted in different directions and uncertainties in the Hounsfiled number is included to see if the target will still receive the intended dose if the patient moves, for example. The different grayscale lines in the top right represent different organs at risk. In this case the bladder (second grayscale line 1102), rectum (third grayscale line 1103) and femoral heads (fourth and fifth grayscale lines 1104, 1105). This shows that arc plans will not give more dose to the bladder and rectum than current state of the art, but reduce femoral head dose. The isodose lines, just show the dose distribution for each level inside the patient. FIGS. 11C-11D illustrates sample results of example treatments of a target region using an energy modulator device according to an embodiment. In FIGS. 11C-11D, water equivalent depth of proton beams are shown, demonstrating an embodiment of the SOBP possible with use of the energy modulator device. As discussed above, FIGS. 11C-11D show movement of 8.63 cm in 4 seconds, wherein the frame rate was 250 mHz. The example in FIGS. 11C-D demonstrates a movement of 1.1 cm can occur in 0.5 seconds, in one example.

4. Computational Hardware Overview

FIG. 12 is a block diagram that illustrates a computer system 1200 upon which an embodiment of the invention may be implemented. Computer system 1200 includes a communication mechanism such as a bus 1210 for passing information between other internal and external components of the computer system 1200. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 1200, or a portion thereof, constitutes a means for performing one or more steps of one or more methods described herein.

A sequence of binary digits constitutes digital data that is used to represent a number or code for a character. A bus 1210 includes many parallel conductors of information so that information is transferred quickly among devices coupled to the bus 1210. One or more processors 1202 for processing information are coupled with the bus 1210. A processor 1202 performs a set of operations on information. The set of operations include bringing information in from the bus 1210 and placing information on the bus 1210. The set of operations also typically include comparing two or more units of information, shifting positions of units of information, and combining two or more units of information, such as by addition or multiplication. A sequence of operations to be executed by the processor 1202 constitutes computer instructions.

Computer system 1200 also includes a memory 1204 coupled to bus 1210. The memory 1204, such as a random access memory (RAM) or other dynamic storage device, stores information including computer instructions. Dynamic memory allows information stored therein to be changed by the computer system 1200. RAM allows a unit of information stored at a location called a memory address to be stored and retrieved independently of information at neighboring addresses. The memory 1204 is also used by the processor 1202 to store temporary values during execution of computer instructions. The computer system 1200 also includes a read only memory (ROM) 1206 or other static storage device coupled to the bus 1210 for storing static information, including instructions, that is not changed by the computer system 1200. Also coupled to bus 1210 is a non-volatile (persistent) storage device 1208, such as a magnetic disk or optical disk, for storing information, including instructions, that persists even when the computer system 1200 is turned off or otherwise loses power.

Information, including instructions, is provided to the bus 1210 for use by the processor from an external input device 1212, such as a keyboard containing alphanumeric keys operated by a human user, or a sensor. A sensor detects conditions in its vicinity and transforms those detections into signals compatible with the signals used to represent information in computer system 1200. Other external devices coupled to bus 1210, used primarily for interacting with humans, include a display device 1214, such as a cathode ray tube (CRT) or a liquid crystal display (LCD), for presenting images, and a pointing device 1216, such as a mouse or a trackball or cursor direction keys, for controlling a position of a small cursor image presented on the display 1214 and issuing commands associated with graphical elements presented on the display 1214.

In the illustrated embodiment, special purpose hardware, such as an application specific integrated circuit (IC) 1220, is coupled to bus 1210. The special purpose hardware is configured to perform operations not performed by processor 1202 quickly enough for special purposes. Examples of application specific ICs include graphics accelerator cards for generating images for display 1214, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 1200 also includes one or more instances of a communications interface 1270 coupled to bus 1210. Communication interface 1270 provides a two-way communication coupling to a variety of external devices that operate with their own processors, such as printers, scanners and external disks. In general the coupling is with a network link 1278 that is connected to a local network 1280 to which a variety of external devices with their own processors are connected. For example, communication interface 1270 may be a parallel port or a serial port or a universal serial bus (USB) port on a personal computer. In some embodiments, communications interface 1270 is an integrated services digital network (ISDN) card or a digital subscriber line (DSL) card or a telephone modem that provides an information communication connection to a corresponding type of telephone line. In some embodiments, a communication interface 1270 is a cable modem that converts signals on bus 1210 into signals for a communication connection over a coaxial cable or into optical signals for a communication connection over a fiber optic cable. As another example, communications interface 1270 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 1270 sends and receives electrical, acoustic or electromagnetic signals, including infrared and optical signals, which carry information streams, such as digital data.

The term computer-readable medium is used herein to refer to any medium that participates in providing information to processor 1202, including instructions for execution. Such a medium may take many forms, including, but not limited to, non-volatile media, volatile media and transmission media. Non-volatile media include, for example, optical or magnetic disks, such as storage device 1208. Volatile media include, for example, dynamic memory 1204. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 1202, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 1202, except for carrier waves and other signals.

Logic encoded in one or more tangible media includes one or both of processor instructions on a computer-readable storage media and special purpose hardware, such as ASIC 1220.

Network link 1278 typically provides information communication through one or more networks to other devices that use or process the information. For example, network link 1278 may provide a connection through local network 1280 to a host computer 1282 or to equipment 1284 operated by an Internet Service Provider (ISP). ISP equipment 1284 in turn provides data communication services through the public, world-wide packet-switching communication network of networks now commonly referred to as the Internet 1290. A computer called a server 1292 connected to the Internet provides a service in response to information received over the Internet. For example, server 1292 provides information representing video data for presentation at display 1214.

The invention is related to the use of computer system 1200 for implementing the techniques described herein. According to one embodiment of the invention, those techniques are performed by computer system 1200 in response to processor 1202 executing one or more sequences of one or more instructions contained in memory 1204. Such instructions, also called software and program code, may be read into memory 1204 from another computer-readable medium such as storage device 1208. Execution of the sequences of instructions contained in memory 1204 causes processor 1202 to perform the method steps described herein. In alternative embodiments, hardware, such as application specific integrated circuit 1220, may be used in place of or in combination with software to implement the invention. Thus, embodiments of the invention are not limited to any specific combination of hardware and software.

The signals transmitted over network link 1278 and other networks through communications interface 1270, carry information to and from computer system 1200. Computer system 1200 can send and receive information, including program code, through the networks 1280, 1290 among others, through network link 1278 and communications interface 1270. In an example using the Internet 1290, a server 1292 transmits program code for a particular application, requested by a message sent from computer 1200, through Internet 1290, ISP equipment 1284, local network 1280 and communications interface 1270. The received code may be executed by processor 1202 as it is received, or may be stored in storage device 1208 or other non-volatile storage for later execution, or both. In this manner, computer system 1200 may obtain application program code in the form of a signal on a carrier wave.

Various forms of computer readable media may be involved in carrying one or more sequence of instructions or data or both to processor 1202 for execution. For example, instructions and data may initially be carried on a magnetic disk of a remote computer such as host 1282. The remote computer loads the instructions and data into its dynamic memory and sends the instructions and data over a telephone line using a modem. A modem local to the computer system 1200 receives the instructions and data on a telephone line and uses an infra-red transmitter to convert the instructions and data to a signal on an infra-red carrier wave serving as the network link 1278. An infrared detector serving as communications interface 1270 receives the instructions and data carried in the infrared signal and places information representing the instructions and data onto bus 1210. Bus 1210 carries the information to memory 1204 from which processor 1202 retrieves and executes the instructions using some of the data sent with the instructions. The instructions and data received in memory 1204 may optionally be stored on storage device 1208, either before or after execution by the processor 1202.

FIG. 13 illustrates a chip set 1300 upon which an embodiment of the invention may be implemented. Chip set 1300 is programmed to perform one or more steps of a method described herein and includes, for instance, the processor and memory components described with respect to FIG. 12 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 1300, or a portion thereof, constitutes a means for performing one or more steps of a method described herein.

In one embodiment, the chip set 1300 includes a communication mechanism such as a bus 1301 for passing information among the components of the chip set 1300. A processor 1303 has connectivity to the bus 1301 to execute instructions and process information stored in, for example, a memory 1305. The processor 1303 may include one or more processing cores with each core configured to perform independently. A multi-core processor enables multiprocessing within a single physical package. Examples of a multi-core processor include two, four, eight, or greater numbers of processing cores. Alternatively or in addition, the processor 1303 may include one or more microprocessors configured in tandem via the bus 1301 to enable independent execution of instructions, pipelining, and multithreading. The processor 1303 may also be accompanied with one or more specialized components to perform certain processing functions and tasks such as one or more digital signal processors (DSP) 1307, or one or more application-specific integrated circuits (ASIC) 1309. A DSP 1307 typically is configured to process real-world signals (e.g., sound) in real time independently of the processor 1303. Similarly, an ASIC 1309 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 1303 and accompanying components have connectivity to the memory 1305 via the bus 1301. The memory 1305 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 1305 also stores the data associated with or generated by the execution of one or more steps of the methods described herein.

5. Alterations, Extensions and Modifications

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article.

What is claimed is:

1. A method for particle therapy comprising:
receiving first data indicating a plurality of target volumes within a target region inside a subject for particle therapy, the first data indicating the plurality of target volumes relative to a particle beam outlet on a gantry for directing a particle beam from the particle beam outlet;
moving automatically one or more energy modulator components of an energy modulator device disposed between the particle beam outlet and the subject, to reduce an energy of the particle beam such that a Bragg Peak is delivered to at least one target volume of the plurality of target volumes;
repeating the step of moving automatically the one or more energy modulator components as the particle beam outlet rotates with the gantry around the subject without changing energy of the particle beam at the particle beam outlet until every target volume is subjected to a Bragg Peak; and
initiating a vibrating component to vibrate the one or more energy modulator components during a delivery of a plurality of particle beams to a target volume to spread depth of the Bragg Peak over at least a subset plurality of target volumes of the plurality of target volumes.

2. The method of claim 1, wherein the initiating step comprises vibrating the one or more energy modulator components at a frequency in a range between about 10 hertz and 1 kilohertz.

3. The method of claim 1, wherein the method further comprises:
manipulating a couch position to effect deposition of a Bragg Peak within the target region.

4. The method of claim 1, further comprising determining on a processor a spatial placement of the one or more of the plurality of energy modulator components relative to one another to effect deposition of the Bragg peak within the at least one target volume of the plurality of target volumes.

5. The method of claim 1, further comprising determining on a processor a spatial placement of Bragg Peaks, a position of one or more of the plurality of energy modulator components, and a delivered dose within the target region.

6. The method of claim 1, further comprising receiving second data indicating a desired dose in the target region.

7. The method of claim 6, further comprising determining on a processor, based on at least the first data and the second data, whether a treatment is complete.

8. A non-transitory computer-readable medium carrying one or more sequences of instructions for execution by one or more processors, wherein execution by the one or more processors causes the one or more processors to:
receive first data indicating a plurality of target volumes within a target region inside a subject for particle therapy, the first data indicating the plurality of target volumes relative to a particle beam outlet on a gantry for directing a particle beam from the particle beam outlet;
move automatically one or more energy modulator components of an energy modulator device disposed between the particle beam outlet and the subject, to reduce an energy of the particle beam such that a Bragg Peak is delivered to at least one target volume of the plurality of target volumes;

repeat the step of moving automatically the one or more energy modulator components as the particle beam outlet rotates with the gantry around the subject without changing energy of the particle beam at the particle beam outlet until every target volume is subjected to a Bragg Peak; and initiate a vibrating component to vibrate the one or more energy modulator components during a delivery of a plurality of particle beams to a target volume to spread depth of the Bragg Peak over at least a subset plurality of target volumes of the plurality of target volumes.

9. A system for particle therapy comprising:

a gantry with a particle beam outlet for directing a particle beam;

an energy modulator comprising one or more energy modulator components disposed between the particle beam outlet and a subject;

a vibrating component configured to vibrate the one or more energy modular components; and at least one processor; and at least one memory including one or more sequences of instructions, the at least one memory and the one or more sequences of instructions configured to, with the at least one processor, cause the system to perform at least the following, receive first data indicating a plurality of target volumes within a target region inside the subject for particle therapy, the first data indicating the plurality of target volumes relative to the particle beam outlet;

move automatically the one or more energy modulator components of the energy modulator, to reduce an energy of the particle beam such that a Bragg Peak is delivered to at least one target volume of the plurality of target volumes;

repeat the step of moving automatically the one or more energy modulator components as the particle beam outlet rotates with the gantry around the subject without changing the energy of the particle beam at the particle beam outlet until every target volume is subjected to a Bragg Peak; and initiate the vibrating component to vibrate the one or more energy modulator components during a delivery of a plurality of particle beams to a target volume to spread depth of the Bragg Peak over at least a subset plurality of target volumes of the plurality of target volumes.

\* \* \* \* \*